United States Patent [19]

Cobb et al.

[11] Patent Number: 4,770,043

[45] Date of Patent: Sep. 13, 1988

[54] MONITORING THE STABILITY OF SOLIDS CONTAINING SUSPENSIONS AND THE LIKE

[75] Inventors: Wesley N. Cobb, University Heights, Ohio; Anthony L. Tuno, Wayne, Pa.

[73] Assignee: The Standard Oil Company, Cleveland, Ohio

[21] Appl. No.: 140,954

[22] Filed: Dec. 24, 1987

Related U.S. Application Data

[63] Continuation of Ser. No. 944,338, Dec. 18, 1986, abandoned.

[51] Int. Cl.⁴ ............................................. G01N 29/02
[52] U.S. Cl. ..................................... 73/597; 73/32 A; 73/61.4
[58] Field of Search ................ 73/597, 32 A, 61.4, 73/61 R

[56] References Cited

U.S. PATENT DOCUMENTS

| | | | |
|---|---|---|---|
| 2,668,365 | 2/1954 | Hogin | 73/32 A |
| 2,978,899 | 4/1961 | Kritz | 73/24 |
| 3,028,749 | 4/1962 | Welkowitz | 73/32 A |
| 3,514,217 | 5/1970 | Reiss. | |
| 3,529,153 | 9/1970 | Zimmerman et al. | |
| 3,648,513 | 3/1972 | Patterson | 73/597 X |
| 3,896,660 | 7/1975 | Valentyik | 73/61.4 |
| 3,911,726 | 10/1975 | Georgiev | 73/32 A |
| 4,002,053 | 1/1977 | Hayakawa | 73/32 R |
| 4,007,319 | 2/1977 | Weisser et al. | 526/60 |
| 4,041,502 | 8/1977 | Williams et al. | 346/33 A |
| 4,140,007 | 2/1979 | Bosland et al. | 73/61.4 |
| 4,235,099 | 11/1980 | Ishizaka | 73/32 A |
| 4,261,196 | 4/1981 | Scheid, Jr. | 73/32 R |
| 4,297,608 | 10/1981 | Jensen | 310/335 |
| 4,414,841 | 11/1983 | Porenski, Jr. et al. | 73/61 R |
| 4,442,700 | 4/1984 | Swoboda | 73/32 A |
| 4,506,541 | 3/1985 | Cunningham | 73/32 R |
| 4,522,068 | 6/1985 | Smith | 73/597 X |
| 4,527,420 | 7/1985 | Foote | 73/61 R |

FOREIGN PATENT DOCUMENTS

| | | | |
|---|---|---|---|
| 476498 | 1/1976 | U.S.S.R. | 73/61 R |
| 1185224 | 10/1985 | U.S.S.R. | 73/597 |

OTHER PUBLICATIONS

Chen, C, et al. Three-Transducer Differential Phase--Shift Method for Measurement of Ultrasonic Velocity in Liquids. In. Rev. Sci. Instr. vol. 46 (8): pp. 1095-1098, Aug. 1975.

Primary Examiner—Stewart J. Levy
Assistant Examiner—Joseph W. Roskos
Attorney, Agent, or Firm—Dilworth & Barrese

[57] ABSTRACT

Suspensions, liquid emulsions and the like are monitored with ultrasonic waves from bottom to top of a column of such to determine if there has been alteration in the original compositions thereof, the method being particularly adapted for determining the stability of coal-aqueous slurries.

12 Claims, 2 Drawing Sheets

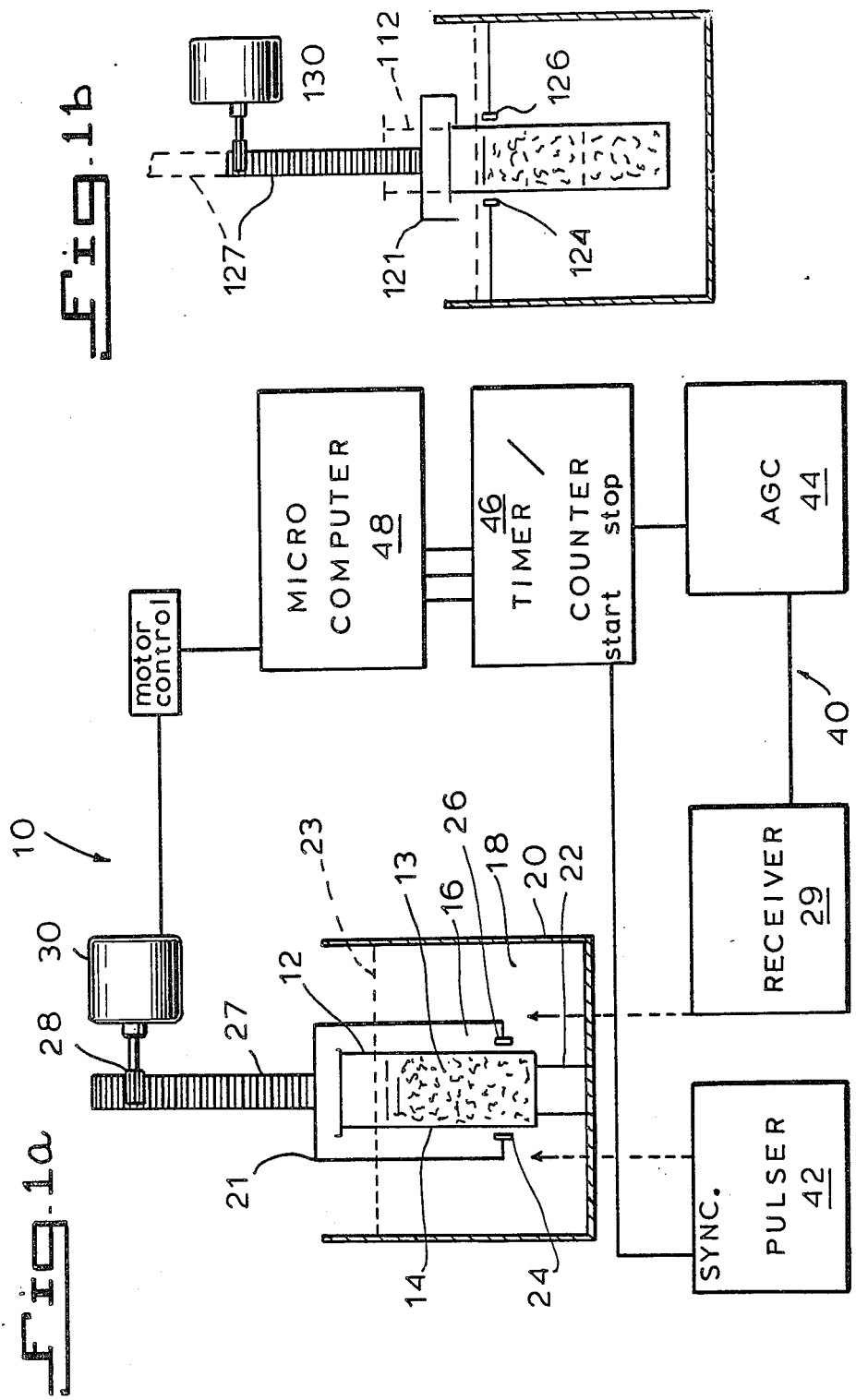

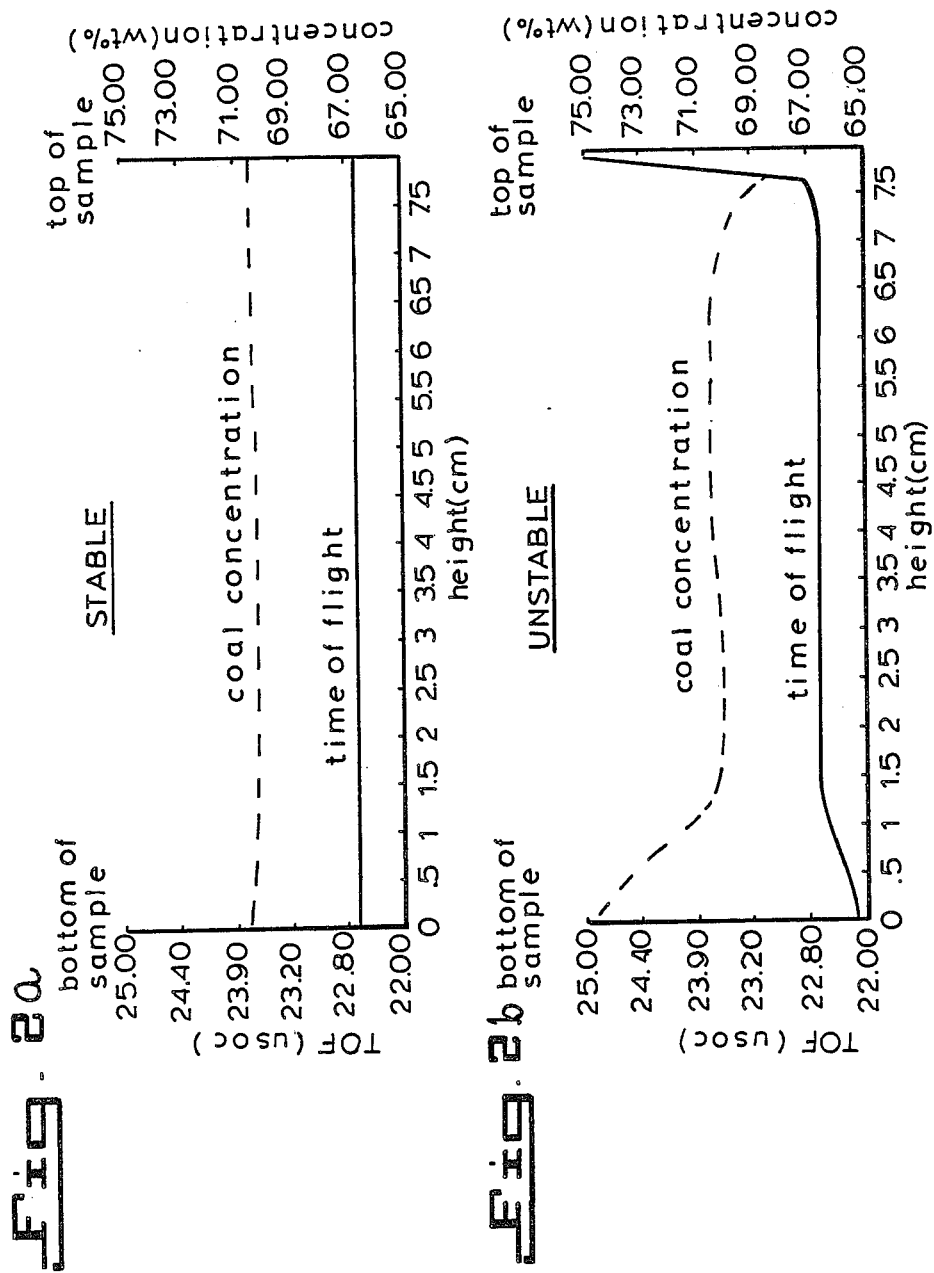

MONITORING THE STABILITY OF SOLIDS CONTAINING SUSPENSIONS AND THE LIKE

This is a continuation of co-pending application Ser. No. 944,338 filed on Dec. 18, 1986, now abandoned.

BACKGROUND OF THE INVENTION

The present invention relates to a method for the monitoring of suspensions, liquid emulsions, mixtures and the like to determine if change in relative component concentration has occurred therein. It is particularly applicable to the monitoring of coal-aqueous slurries to determine if coal settlement has taken place in such slurries.

It is important that certain characteristics of liquids, suspensions and the like be monitored for various purposes. For that reason certain monitoring methods and apparatus by which monitoring can be effected heretofore have been developed. For example, U.S. Pat. No. 4,041,502 describes measuring sedimentation in blood samples by passing light wave energy through a glass tube enclosed column of the sample and recording that signal in such manner as to provide a plot of the changing location within the sample of the separation boundary between blood cells and clear plasma fluid. U.S. Pat. No. 4,442,700 uses ultrasonic wave pulsing through the casing of a lead-acid battery to determine specific quantity (density) of the electrolyte therein and hence indication of the serviceability of the battery. U.S. Pat. Nos. 3,028,749 and 3,911,726 also describe ultrasonic procedures for determining various parameters, e.g., density, of liquids as does U.S. Pat. No. 4,235,099 which relates to a method and apparatus particularly useful for liquids specific gravity mensuration in medical and related activities. U.S. Pat. No. 4,007,319 describes use of electrical conductance for monitoring a suspension polymerization reaction so as to anticipate for corrective counteraction thereto, of the onset of reaction conditions that signal incipient failure of suspension formation.

Other patents which deal with aspects of product monitoring as related to density, sedimentation and analogous considerations include U.S. Pat. Nos. 2,668,365; 2,715,831; 2,825,698; 2,978,899; 3,514,217; 3,529,153; 3,896,660; 3,964,037; 4,007,315; 4,002,053; 4,041,500; 4,047,891; 4,048,844; 4,140,007; 4,261,196; 4,297,608; 4,466,272; 4,487,278; 4,506,541 and 4,527,420.

Those skilled in the art readily understand the wide range of potential applications for suspension, emulsion and mixture monitoring in various industries such as food, pharmaceuticals, minerals processing, waste treatment, paper, etc. Another area of special applicability for such monitoring is in respect to coal fuels wherein the ready facility for monitoring coal slurries used, e.g., for fuel purposes is desirable so that determination of optimized thickener and surfactant amounts to be added to a fuel slurry at production thereof to insure long term stability, are ascertainable. U.S. Pat. No. 4,441,889 describes a coal-in-aqueous slurry form wherein additive materials such as surfactants, stabilizing agents, thickeners, etc., are employed to disperse and stabilize the coal to high solids concentrations of 70% by weight, or higher. These mixtures are free-flowing, have excellent long term storage stability and being in fluid form, can be burned in apparatus normally used for burning fuel oil. Since these coal-aqueous slurries generally will be stored for some time prior to use for their intended purposes any sedimentation which might occur therein would be undesirable when the mixture was later used in a fuel burning operation such as in a boiler. By monitoring over a period of time representative samples of the slurries taken from production runs, the long term stability of the slurries are learned as is data useful for compensating in future production for any instability noted in monitored prior produced coal-aqueous slurries of given coal solids concentration.

It is therefore desirable that a highly effective, yet simple method be provided for monitoring the solids concentration of coal-aqueous slurries and the like and by non-destructive procedure and under the natural conditions which such slurries subsist from time of production until ultimate end use thereof.

SUMMARY OF THE INVENTION

An object of the invention is to provide a method for monitoring the stability of solids-containing suspensions, liquid emulsions and the like. It is particularly concerned with the monitoring of the stability of coal-aqueous slurries.

Another object of the invention is to provide a method for monitoring the stability of solids-containing suspensions, liquid emulsions, etc., in manner non-destructive of the suspension and wherein the monitoring is of a representative suspension sample drawn at production from an industrial production run so that data obtained from the sample is reflective of the stability character of the industrial suspension stocks.

A further object is to provide a suspension stability monitoring method wherein the sample is confined in a holder, rapidly monitored in a matter of a minute or so to obtain data and then conveniently stored for further monitoring at subsequent times, all this being done without any destructive effect on the sample or causative of any change in character of the suspension.

In accordance with the invention, the solids-containing suspension in requisite column sample quantity thereof is confined in a holder made of material having good sonic transmissivity and the holder is then disposed in a liquid bath, the liquid being one having a density substantially near or at that of the suspension, e.g., water. A transmitting transducer is positioned at one side of the holder and a receiving transducer at an opposite side, the two transducers being mechanically connected together to allow for unitary vertical movement of the two up and down alongside the holder. Alternatively, the two transducers can be fixed and the suspension holder can be reciprocated vertically relative to the transducers. Ultrasonic waves are pulsed through the suspension at elevations between the two vertical extremes of such column by the transmitting transducer as relative movement between the transducers and the holder is effected, and these waves are detected by the receiving transducer after they have passed through the suspension. The detected sound waves are converted to electrical signals indicative of the sonic wave time-of-flight through the suspension.

Since the time-of-flight of sound waves propagated through a stable suspension of a given solids concentration such as a 70% coal solids coal-aqueous slurry can be determined, this data serves as a comparative to which the electrical signals obtained from the sample can be applied and thus deviation therefrom noted so that deviation would signal or indicate alteration of the solids concentration from a desired level, i.e., occurrence of sedimentation exists in the sample. Known time-of-flight data can be obtained from stable suspensions of solids concentrations over a range of such concentrations and thus when sample signals which show deviation are obtained, the quantum of change in solids concentration from the desired level is readily ascertained.

In accordance with the invention, the electrical signals obtained from sonic pulsing of the sample can be applied to produce a visual plot of the time-of-flight data and the plot reflective of time-of-flight values from bottom to top of the column will indicate by presence of or lack of linearity, the stability condition of the coal-aqueous slurry.

The testing of the sample can be carried out very quickly in about one minute inasmuch as a sample column of (preferably a rectangular section column) about $\frac{1}{4}$ to $\frac{1}{2}$ inch depth, 4 inch width and height of about 3 to about 4 inches is all that is needed.

The invention accordingly comprises the features and arrangements of steps for monitoring the stability of suspensions as will be exemplified in the description hereinafter set forth and the scope of the invention will be indicated in the claims.

BRIEF DESCRIPTION OF THE DRAWINGS

A fuller understanding of the nature and objects of the invention will be had from the following detailed description taken in conjunction with the accompanying drawings, in which:

FIG. 1a is a schematic showing of apparatus with which solids-containing suspensions can be monitored in accordance with the principles of the present invention and wherein the sample is held fixed in the liquid bath and the transducers are moved up and down alongside the sample holder;

FIG. 1b is a fragmentary showing of the FIG. 1a apparatus but in an embodiment wherein the transducers are fixed and the holder and hence the sample suspension contained therein is moved relative to the transducers;

FIG. 2a is a plot showing time-of-flight and coal concentration values as obtained along various bottom to top levels in a sample column of a stable coal-aqueous slurry containing a 70% coal concentration which was stored for a period after draw off from a production run; and FIG. 2b is a plot of an unstable coal-aqueous slurry sample obt-ianed from monitoring such sample after the same storage period and this sample having been obtained from another production run.

Throughout the description like reference numerals are used to denote like parts in the drawings.

DESCRIPTION OF THE PREFERRED EMBODIMENT

The apparatus 10 shown in FIG. 1a with which the present invention can be practiced is the same as that described and claimed in the commonly owned concurrently filed application of Wesley N. Cobb, Ser. No. 944,326 entitled "Suspension Stability Monitoring Apparatus" the disclosure of which is hereby incorporated by reference.

A sample holder 12 which may be fitted with a cover (not shown) contains a sample column 13 of coal-aqueous slurry which sample had been drawn from a production run source of slurry, the coal solids concentration of which has a value of 70% although it will be understood that such product can be made with various and other intended coal solids concentrations. The sample in the holder is intended to be stored, monitored, returned to storage, monitored again, etc., for as long as it can be expected that the production run commercial product material may subsist in storage until put to final end use so that the ongoing monitoring of the sample is reflective of the stability condition of the commercial product. The sample holder 12 preferably is made of a thermoplastic material to provide good sonic transmissivity, glass, e.g., not being as acoustically transparent as most thermoplastics. The use of thermoplastic allows the passage of ultrasonic waves through the holder without great attenuation or reflection thereof. The holder can be of rectangular profile having, e.g., spaced parallel side walls 14, 16 which measure about 5" high, slightly more than 4" wide, and slightly more than $\frac{1}{2}$" in depth so that a coal slurry column about 4"×3" by about $\frac{1}{4}$" to $\frac{1}{2}$" can be confined therein. For monitoring purposes a relatively narrow depth sample only is required.

The sample containing holder 12 is placed in a liquid bath 18, the bath being contained in a suitable vessel 20 and the holder supported in suitable manner as on pedestal 22 although any other types of container support could be used. The arrangement is such that the bath level 23 is above the sample level. The bath 18 is selected to be a liquid having a density substantially near or at that of the coal aqueous slurry and conveniently can be water.

A sonic head frame 21 carries on depending structure thereof, a transmitting transducer 24 and a receiving transducer 26, these two devices being disposed adjacent the respective two side walls 14, 16 of the container and being reciprocally aligned one with the other. Head frame 21 is fixed to means with which the frame can be straight line vertically moved up and down to allow for ultrasonic monitoring of the coal aqueous slurry sample between the two vertical extremes thereof. Such means could be a rack 27 attached to the head frame and in mesh with pinion 28, the pinion being driven by a control motor 30 that reversibly drives the pinion to produce the required up and down movement of the head frame.

In FIG. 1a, the operative control arrangement for the apparatus is shown in block diagram form generally at 40. Pulse generator 42 is used to energize transmitting transducer 24 so that device generates short duration (e.g., 1 microsecond) ultrasonic waves that pass through the sample 13 and are received by the receiving transducer 26 so that these receptions are converted to electrical signals which as output from receiver 29 are fed to an automatic gain circuit 44. The automatic gain circuit 44 serves to limit the received signal voltage to an amplitude of e.g., one volt to compensate for any ultrasonic attenuation changes in the sample. Upon initiation of each sound pulse by transducer 24, timer/counter unit 46 starts counting and when the sound pulse is received by transducer 26 and the converted electrical signal therefrom exceeds a set or threshold value (e.g., 0.1 volt), the timer/counter 46 is stopped, the interval between start and stop being the time-of-flight of the pulsed sound wave through the sample and bath medium between the transducers. Microprocessor unit 48 acquires this time-of-flight data and processes same to provide solids-concentration information, e.g., as a control output which serves to operate a visual recording device representing time-of-flight and/or solids concentration in plot form as shown in FIGS. 2a and 2b.

As shown in FIG. 1b and instead of vertically moving the transducers, the transducers could be fixed and the sample moved. Thus transducers 124, 126 are mounted in fixed positions alongside holder 112 and the holder in turn is supported by head frame 121. When motor 130 is operated, pinion 128 will reciprocate rack 127 and hence the frame connected therewith so that the sample holder moves up or down to position the aqueous slurry column at various successive levels thereof alongside the transducers for monitoring the full column height.

In monitoring the sample, it is required to determine if any solids concentration changes due to settling have occurred at any location therein so that monitoring is carried out along the entire vertical expanse of the sample column. For that reason, the monitoring procedure will be started at one end, preferably the bottom end, of the sample. Microprocessor unit 48 can be employed to control the drive of motor 30 to operate movement of the sonic head frame 21 upwardly from the bottom to the top of the column in a time period of about one minute and during which period monitoring will be taking place at successive ones of elevations in the coal aqueous slurry between zero and maximum (sample level) elevations thereof. Alternatively motor 130 can be operated to lower or raise holder 112 to effect monitoring as shown by the FIG. 1b embodiment. The time-of-flight information retrieved at these successive ones of the elevations indicate concentration and such data can be employed to plot the stability condition of the coal aqueous slurry sample at the various elevations. Linearity of the plot or a lack thereof provides immediate visual graphic display of stability.

FIGS. 2a and 2b show respective plots of stable (initial approximately 70% solids) and unstable (initially approximately 67% solids) coal aqueous slurry samples each stored at the same time and then monitored for stability one day later. The FIG. 2a stable sample plot shows substantial linearity in both the time-of-flight and coal concentrations curves and general constancy of these values at all elevations in the coal aqueous slurry sample from bottom to top thereof. The FIG. 2b plot on the other hand shows that significant settling already has taken place in that sample. Thus it will be seen that a layer of high solids concentration (about 75%) has formed at the bottom of the sample as compared to the initial 67% solids concentration value. In addition, the low solids concentration at the top of the sample indicates the formation of a low-solids, surface water layer of about 0.5 cm height in the sample.

Continued and subsequent monitoring of samples can be carried out. For example, continued monitoring of the FIG. 2a sample could be carried out during successive periods of days and weeks to confirm the indicated stable character of that coal aqueous slurry. The FIG. 2b sample also could be subsequently monitored to ascertain the rate of sedimentation happening since that data then becomes useful in terms of how like compositioned production run coal aqueous slurry can more effectively be stabilized with additives, etc., at the time of production to prevent sedimentation occurring during the expected coal aqueous slurry subsistence before final end use thereof.

In regard to simply and effectively ascertaining the coal aqueous slurry concentration of samples, the graphic plot procedure in FIGS. 2a and 2b optimizes this end. Thus in the plot recorder, time-of-flight data and aqueous slurry coal concentrations represent ordinates of the plot while the abscissa represents various height levels in the sample from bottom to top. These data therefore provide the most graphic indication of a particular sample condition plot inasmuch as the plotted data for coal concentration and time-of-flight need only be compared to the straight line abscissa as a reference datum and the closeness or departure of the plotted data with the abscissa in linearity shows sample condition.

An important advantage of the invention is the facility with which samples can be monitored, returned to storage and subsequently monitored again. The samples once placed in the holder 12 need not be disturbed since they remain in the holder for monitoring under the same natural conditions applicable to commercial product storage, there is no disturbance of the samples and monitoring can be carried out at the same temperature each time.

While there is above disclosed only certain embodiments of the present invention it will be apparent that variations made be made therein by those skilled in the art without departing from the scope of the inventive concept disclosed.

What is claimed is:

1. A method for monitoring the stability of a solids-containing suspension or the like to determine if the solids concentration thereof has altered from a desired value due to settlement of solids within the suspension, said method comprising confining a column of said suspension in a holder made from a material having good sonic transmissivity, providing a liquid bath in which the holder can be disposed, generating ultrasonic waves through the suspension from one side of the holder and at a succession of the elevations between the vertical extremes of the suspension column therein and while the successive ones of said elevations are submerged below the level of the bath, detecting the ultrasonic waves at an opposite side of the holder after they have passed through the suspension and converting the wave detections to electrical signals indicative of the wave time-of-flight through the suspension, the electrical signals being recorded as a visual plot of such signals, and comparing such signals with known values of same representing the desired solids concentration to determine if settlement indicative deviation of such signals from the known values exists the visual plot being one wherein the time-of-flight electrical signals are recorded at ordinate graphic locations in correspondence to abscissa locations associated with the successive column bottom-to-top elevations to generate the line plot whereby the presence or absence of linearity in said line plot as compared to a straight line abscissa datum denotes respective stable/unstable suspension condition.

2. The method of claim 1 in which the holder is disposed stationary in the liquid bath with the level of the suspension in the holder below the bath level and the generation and detection of the ultrasonic waves is effected with means moveable vertically alongside the holder.

3. The method of claim 1 in which the holder is moved vertically in the bath and past ultrasonic wave generation and detection means fixed at a submerged location in said bath.

4. The method of claim 1 in which the liquid in the bath is one having a density substantially near or at that of said suspension.

5. The method of claim 4 in which the bath liquid is water.

6. The method of claim 1 in which the suspension is a coal-aqueous slurry.

7. The method of claim 6 in which the solids concentration of the suspension is about 70% by weight coal.

8. The method of claim 6 in which the column of suspension is of a narrow depth as compared to the width and height thereof.

9. The method of claim 8 in which the column of suspension has a depth of about ¼ inch to about ½ inch.

10. The method of claim 9 in which the width of said column is about 4 inches and the height about 3 to about 4 inches.

11. The method of claim 1 in which the holder is made of thermoplastic material.

12. The method of claim 1 in which the ultrasonic waves are generated at a succession of locations from bottom to top of the suspension column.

* * * * *

UNITED STATES PATENT AND TRADEMARK OFFICE
CERTIFICATE OF CORRECTION

PATENT NO. : 4,770,043
DATED : September 13, 1988
INVENTOR(S) : Cobb et al.

It is certified that error appears in the above-identified patent and that said Letters Patent is hereby corrected as shown below:

On the face page, under OTHER PUBLICATIONS insert:

--"Technique To Measure Emulsion Creaming By Velocity of Ultrasound" by Howe et al., J. Dispersion Science and Technology, 7(2), 231-243 (1986) (Received Oct. 7, 1985).-- and

--"Ultrasonic Technique For Dispersed-Phase Holdup Measurements" by Bonnet et al., Ind. Eng. Chem. Res. 1987 (received for review August 20, 1985, accepted November 3, 1986), 26, 811-815.--

Column 3, line 10, "time-of-fli-ght" should be --time-of-flight--; and,
Column 3, line 48, "obt-ianed" should be -- obtained --.

Signed and Sealed this

Fourteenth Day of March, 1989

Attest:

DONALD J. QUIGG

Attesting Officer

Commissioner of Patents and Trademarks